(12) United States Patent
Charlier, Jr. et al.

(10) Patent No.: US 7,781,412 B2
(45) Date of Patent: Aug. 24, 2010

(54) BIPHENYL INHIBITORS OF CARBONYL REDUCTASE

(75) Inventors: Henry A. Charlier, Jr., Boise, ID (US); Christopher K. Ewing, Boise, ID (US)

(73) Assignee: Boise State University, Boise, ID (US)

( * ) Notice: Subject to any disclaimer, the term of this patent is extended or adjusted under 35 U.S.C. 154(b) by 0 days.

(21) Appl. No.: 11/863,243

(22) Filed: Sep. 27, 2007

(65) Prior Publication Data

US 2008/0227731 A1 Sep. 18, 2008

Related U.S. Application Data

(63) Continuation-in-part of application No. 11/711,490, filed on Feb. 26, 2007.

(60) Provisional application No. 60/776,269, filed on Feb. 24, 2006.

(51) Int. Cl.
| | |
|---|---|
| A01N 43/04 | (2006.01) |
| A01N 29/04 | (2006.01) |
| A01N 29/10 | (2006.01) |
| A01N 27/00 | (2006.01) |
| A61K 31/70 | (2006.01) |
| A61K 31/03 | (2006.01) |
| A61K 31/025 | (2006.01) |
| A61K 31/015 | (2006.01) |

(52) U.S. Cl. .................. 514/34; 514/754; 514/755; 514/765

(58) Field of Classification Search .................. 514/34, 514/754, 755, 765
See application file for complete search history.

(56) References Cited

U.S. PATENT DOCUMENTS

| | | | |
|---|---|---|---|
| 3,164,524 A | 1/1965 | Fand et al. | 167/93 |
| 3,170,945 A | 2/1965 | Schisla et al. | 260/463 |
| 3,234,255 A | 2/1966 | Hackmann et al. | |
| 3,300,376 A | 1/1967 | Schisla et al. | 167/30 |
| 3,336,199 A | 8/1967 | Stolar et al. | 167/82 |
| 2006/0009506 A1 * | 1/2006 | Westwick et al. | 514/395 |

FOREIGN PATENT DOCUMENTS

WO  WO 2005/007085 A2  1/2005

OTHER PUBLICATIONS

Definition of "derivative" from the Merriam Webster Online Dictionary [online], [Retrieved on Jan. 7, 2009]. Retrieved from the internet <http://www.merriam-webster.com/dictionary/derivative>.*

Definition of "pseudohalogen" from AllWords.com [online], [Retrieved on Jul. 7, 2009]. Retrieved from the internet <http://www.allwords.com/word-pseudohalogen.html>.*

Goodman and Gilman's The Pharmacological Basis of Therapeutics. editors Joel G. Hardman and Lee E. Limbird, published by The McGraw-Hill Companies, Inc., 2001, p. 54-56.*

Mordente, A., Minotti, g., Martorana, G.E., Silvestrini, A., Giardina, B., Meucci, E. (2003) Anthracycline secondary alcohol metabolite formation in human or rabbit heart: biochemical aspects and pharmacologic implications. Biochemical Pharmacology, vol. 66, p. 989-998.*

Parikh, S., Moynihan, D.P., Xiao, G., Tonge, P.J. (1999) Roles of Tyrosine 158 and Lysine 165 in the Catalytic Mechanism of inhA, the Enoyl-ACP Reductase from *Mycobacterium tuberculosis*. Biochemistry, vol. 38, p. 13623-13634.*

Warren, K.E., McCully, C.M., Walsh, T.J., Balis, F.M. (2000) Effect of Fluconazole on the Pharmacokinetics of Doxorubicin in Nonhuman Primates. Antimicrobial Agents and Chemotherapy, vol. 44, No. 4, p. 1100-1101.*

"Triclosan" from Chemistry Daily [online]., [Retrieved on Jul. 6, 2009]. Retrieved from the internet <http://web.archive.org/web/20050523074758/http://www.chemistrydaily.com/chemistry/Triclosan>.*

Park, S., Gwak, J., Cho, M., Song, T., Won, J., Kim, D.-E., Shin, J.-G., Oh, S. (2006) Hexachlorophene Inhibits Wnt/β-Catenin Pathway by Promoting Siah-Mediated β-Catenin Degradation. Molecular PHarmacology, vol. 70, No. 3, p. 960-966.*

(Continued)

*Primary Examiner*—Shaojia Anna Jiang
*Assistant Examiner*—Scarlett Goon
(74) *Attorney, Agent, or Firm*—Pedersen and Company, PLLC; Ken J. Pedersen; Barbara S. Pedersen

(57) ABSTRACT

Compositions of matter and methods of treating cancer patients may prevent or limit cardiotoxicity during or after chemotherapy, and/or may prevent or lower resistance to anthracycline drugs, both of which are believed to be caused by the human enzyme carbonyl reductase. Thus, the compositions and methods may be used to reduce the dosages of anthracycline anti-cancer drugs necessary to produce a desired cancer-cell-killing performance. Preferred embodiments comprise treating cancer patients with a pharmaceutical composition comprising biphenyl compounds having two halogenated (or pseudo-halogenated) and/or hydroxylated, aryl groups that are linked by a bridging atom. The preferred composition of biphenyl compound(s) may be administered in a pharmaceutical composition also comprising at least one anthracycline compound, or may be administered separately than the at least one anthracycline compound. Especially-preferred biphenyl compounds include triclosan, hexachlorophene, and dichlorophene.

9 Claims, 9 Drawing Sheets

OTHER PUBLICATIONS

Lu, S., Archer, M.C. (2005) Fatty acid synthase is a potential molecular target for the chemoprevention of breast cancer. Carcinogenesis, vol. 26, No. 1, p. 153-157.*

Heath, R.J., Yu, Y.-T., Shapiro, M.A., Olson, E., Rock, C.O. (1998) Broad Spectrum Antimicrobial Biocides Target the FabI Component of Fatty Acid Synthesis. The Journal of Biological Chemistry, vol. 273, No. 46, p. 30316-30320.*

Bacq, et al.; Successful Treatment of Acute Fascioliasis With Bithionol*Hepatology*p. 1; 1991.

"Drugs For Parasitic Infections";*The Medical Letter, Inc*; pp. 1-12; Aug. 2004.

Olson, et al.; "Protection from Doxorubicin-Induced Cardiac Toxicity in Mice with a Null Allele of Carbonyl Reductase": 1*Cancer Research* 63; 6002-6006; Oct. 15, 2003.

Aiken, et al.; "A Cell-Based Screen for Drugs to Treat Huntington's Disease";*Neurobiology of Disease*;16; 546-555; 2004.

Hawn, et al.; "Update on Hepatobiliary and Pulmonary Flukes [Abstract]"*Current Infectious Disease Reports* 1999.

Minotti, et al.; "Anthracyclines: Molecular Advances and Pharmacologic Developments in Antitumor Activity and Cardiotoxicity"; *The American Society for Pharmacology and Experimental Therapeutics*vol. 56, No. 2 185-229; 2004.

Forrest, et al.; "Human Carbonyl Reductase Overexpression in the Heard Adances of the Development of Doxorubicin-induced Cardiotoxicity in Transgenic Mice";*Cancer Research*, 5158-5164; Sep. 15, 2000.

"Bithionol Product Information";*Sigma-Aldrich, Inc*; 2 pages; May 24, 2005.

"2,2'-Sulfinyl-bis (4,6-dichlorophenol) Product Information"; 222. sigmaaldrich.com; May 24, 2005.

Tanaka, et al.; "An Unbiased Cell Morphology -Based Screen for New", Biological Active Small Molecules;*PLoS Biology* 0764-0776; May 2005.

Adolphson, Curtis C, et al: "Response to Doxorubicin and Mitomycin in Cholaniocarinoma": A Case Report Division of Hematology and Oncology,Birmingham, AL, US, May 18, 1981.

Carlquist, Magnus, et al: "Flavonoids as Inhibitors of Human Carbonyl Reductase 1", Chemico-VBiological Interactions 174 (2008), pp. 98-108, Lund, Sweden.

J.P.R. Hartley, et al: "A Case of Clonorchiasis in England", British Medical Journal, Sep. 6, 1975, p. 575.

Kavanagh, K.L., et al: "The SDR Superfamily: Functional and Structural Diversity Within a Family of Metabolic and Regulatory Enzymes", Cellular and Molecular Life Sciences 65 (2008), pp. 3895-3906.

Persson, Bengt, et al: "The SDR (short chain dehydrogenase/reductase and related enzymes) Nomenclature Initiative", Chemico-Biological Interactions 178 (2009) pp. 94-98.

Larkin, M.A,, et al: "Clustal W and Clustal X Version 2.0", Bioinformatics Applications Note, vol. 23 No. 21 2007, pp. 2947-2948, doi:10.1093/bioinformatics/btm404.

Ewing, Christopher K., et al: "Dichlorophene Inhibition of Human Carbonyl Reductase", The Northwest Regional Meeting (Jun. 17-20, 2007).

Slupe, Andrew, et al: "Reduction of 13-Deoxydoxorubicin and Daunorubicinol Anthraquinones by Human Carbonyl Reductase", Cardiovascular Toxicology (2005) 05 365-376.

Remington: "Doxorubicin Hydrochloride", The Science and Practice of Pharmacy, Nineteenth Edition, vol. II.

Williams, et al: "Inhibitors of Human Carbonyl Reductase", Journal of the Idaho Academy of Science, dated Wednesday, Jun. 1, 2005.

Larson, Willaims B, et al: "Abstract", Novel Inhibitors of Carbonyl Reductase: Feb. 2005.

Larson, Williams, B, et al: "Poster Presentation", Novel Inhibitors of Carbonyl Reductase: presented at the 229th ACS National Meeting, in San Diego, CA, Mar. 13-17, 2005.

* cited by examiner

**Arrow designates the carbon at position 13

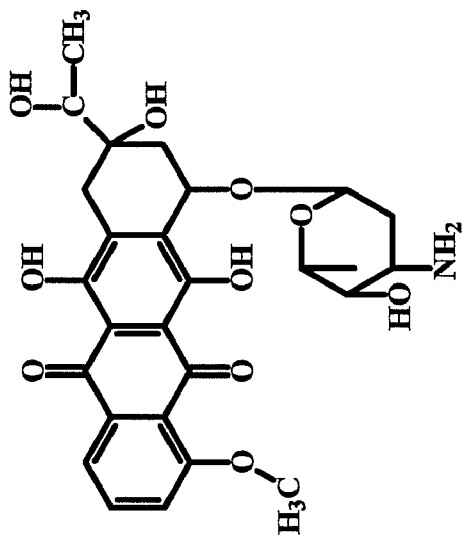
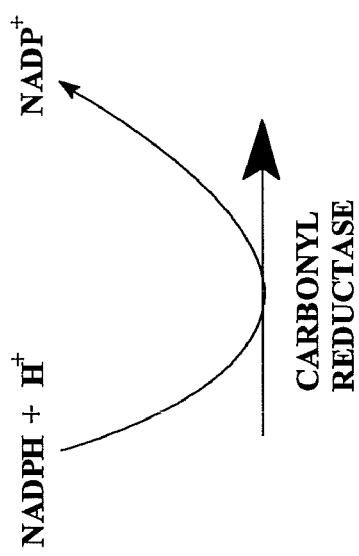
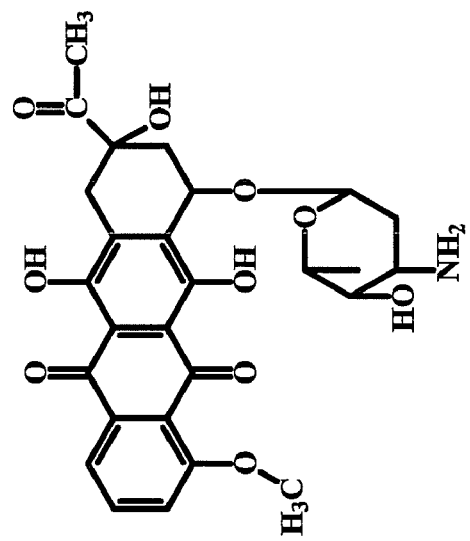
Fig. 2

| Compound | Inhibition Pattern | $K_{is}$, (μM) | $K_{ii}$, (μM) |
|---|---|---|---|
| Hexachlorophene (Fig. 1, C.) | Uncompetitive[a,b] | -- | 12 ± 1 |
| Dichlorophene (Fig. 2, D.). | Noncompetitive[a,c] | 40 ± 8 | 78 ± 8 |
| Dichlorophene (Fig. 2, D.). | Uncompetitive[b,d] | | 20 ± 1 |
| Triclosan (Fig. 3, E.) | Uncompetitive[a,b] | -- | 0.23 ± 0.01 |

[a]Studies were done with a fixed NADPH concentration of 50 μM, varied menadione concentrations ranging from 12 to 125 μM in 100 mM sodium phosphate buffer, pH=7.0.

[b]Data fit best to the uncompetitive inhibition model $v_0 = \dfrac{VA}{A(1+\dfrac{I}{K_{ii}})+K_m}$ where A is the concentration of menadione, I is the inhibitor concentration, V is the maximal velocity, $K_m$ is the Michaelis constant for menadione and $K_{ii}$ is the intercept inhibition constant.

[c]Data fit best to the noncompetitive inhibition model $v_0 = \dfrac{VA}{A(1+\dfrac{I}{K_{ii}})+K_m(1+\dfrac{I}{K_{is}})}$ where A is the concentration of menadione, I is the inhibitor concentration, V is the maximal velocity, $K_m$ is the Michaelis constant for menadione, $K_{ii}$ is the intercept inhibition constant, and $K_{is}$ is the slope inhibition constant.

[d]Study done with a fixed NADPH concentration of 300 μM and varied menadione as previously described.

Fig. 7

BIPHENYL INHIBITORS OF CARBONYL REDUCTASE

Some activities related to this invention were conducted with support by National Institute of Health, NIH/P20RR16454.

BACKGROUND OF THE INVENTION

1. Field of the Invention

This invention relates to compositions of matter, and methods of using said compositions for inhibiting enzyme(s) that destroy the cell-killing efficacy of cancer drugs and/or that catalyze the formation of dangerous or damaging metabolites during or after cancer treatment. More specifically, preferred embodiments of the invented compositions and methods inhibit human carbonyl reductase, thus inhibiting conversion of anthracycline to metabolites that are less effective cell-killing agents and that also lead to cardiotoxicity during or after treatment of cancer patients. Thus, the preferred compositions and methods are believed to lower the amount needed, and the cardiotoxic side-effects, of anthracyclines in cancer treatment.

2. Related Art

Anthracyclines are a family of drugs that are effective anti-neoplastic agents, and are commonly used to treat cancer, including leukemia, soft tissue sarcomas, and breast and lung cancer. Anthracyclines intercalate into DNA and are described as topoisomerase Type II poisons. The anthracycline family comprises adriamycin, daunomycin, daunorubicin, doxorubicin, epirubicin, and idarubicin. See, for example, representations of doxorubicin and daunorubicin in FIG. 1.

While the anthracyclines are known to be potent anti-tumor drugs, their use has been limited due to potentially life-threatening cardiotoxicity associated therewith. This problem may be described as cumulative dose-dependent cardiotoxicity, which can ultimately result in congestive heart failure. There is significant evidence that the toxic effects on the heart associated with anthracycline-based cancer treatment are largely attributable to anthracycline alcohol metabolite(s) that can form and accumulate in cardiac cells. These metabolites are known to disrupt several key processes in heart muscle and thus impair heart function. See, for example, Minotti, et al., "Anthracyclines: Molecular Advances and Pharmacologic Developments in Antitumor Activity and Cardioitoxicity," *Pharmacological Reviews*, 56: 185-229, 2004.

Enzymes belonging to the aldo-keto reductase and short chain dehydrogenase/reductase protein superfamilies catalyze the formation of the anthracycline metabolites. Of these enzymes, carbonyl reductase ("CR") has been specifically linked to the development of anthracycline-induced cardiotoxicity. See, for example, Olson, et al., "Protection from Doxorubicin-Induced Cardiac Toxicity in Mice with a Null Allele of Carbonyl Reductase 1," *Cancer Research*, 63, 6602-6606, Oct. 15, 2003. Findings that support the hypothesis that CR is a key factor in anthracycline-induced cardiotoxicity include studies wherein heart-specific over-expression of human carbonyl reductase in transgenic mice substantially increased the development of cardiotoxicity after anthracycline treatment. See, for example, Forrest, et al., "Human Carbonyl Reductase Overexpression in the Heart Advances the Development of Doxorubicin-induced Cardiotoxicity in Transgenic Mice," *Cancer Research*, 60, 5158-5164, Sep. 15, 2000.

Further, several studies have implicated the reduction of anthracyclines by carbonyl reductase in drug resistance. This is largely because the alcohol metabolites of anthracyclines have been shown to exhibit significantly lowered anticancer properties. Relevant to this are studies performed by Tanaka, et al., (reported in Tanaka, et al., "An Unbiased Cell Morphology-Based Screen for New, Biologically Active Small Molecules," PLoS Biology, Vol. 3, Iss. 5, 0764-0776, May 2005). Tanaka, et al. report that a potent inhibitor of human carbonyl reductase (3-(7-isopropyl-4-(methylamino)-7H-pyrrolo[2,3-d]pyrimidin-5-yl) phenol, when coadministered with daunorubicin to A549 adenocarcinoma cells, was found to enhance the cytotoxicity of daunorubicin. It was concluded that inhibition of carbonyl reductase led to enhanced cytotoxicity of daunorubicin.

See, for example, the FIG. 2 representation of carbonyl reductase catalysis (reduction via $NADPH+H^+$ mechanism) of the anthracycline daunorubicin to daunorubicinol. While daunorubicin is an effective anti-cancer agent by means of its effective disruption of DNA replication, daunorubicinol exhibits reduced anti-cancer properties and is a potent cardiotoxin. Therefore, conversion to the alcohol metabolite not only creates a potent cardiotoxin, but also lowers the efficacy of the treatment for a given amount of anthracycline.

Therefore, the inventor believes that there is a need for pharmaceutical interventions that block the action of human carbonyl reductase. The inventor believes that such pharmaceutical interventions will increase the efficacy of anthracycline therapy in cancer/tumor treatment by preventing or lowering conversion of anthracyclines to less potent cell-killing species and by reducing the risk of cardiotoxicity.

SUMMARY OF THE INVENTION

The present invention comprises compositions of matter that include inhibitors of human enzymes. The preferred embodiments comprise compositions of matter, and methods of treating patients, that prevent or lower conversion in the human body of cancer drugs to metabolites that are less effective for cancer treatment and/or that are believed to produce cardiotoxicity during or after cancer treatment. Hence, by using preferred embodiments of the invented compositions and/or methods, the effectiveness of a given dose of anthracycline drugs may increase, and the risk of cardiotoxicity typically associated with said treatment may lessen.

Embodiments of the invention may comprise compositions or treatments for, and/or methods of, inhibiting one or more enzymes from the groups referred to as aldo-keto reductase and short chain dehydrogenase/reductase protein superfamilies. Preferably, embodiments of the invention comprise compositions or treatments for, and/or methods of, inhibiting enzyme(s) that catalyze anthracycline conversion to anthracycline metabolites, wherein carbonyl reductase ("CR") is especially implicated as described in the Related Art section above. Preferably, this inhibition also has the direct effect of maintaining concentrations of anthracyclines, which are desirable for their cell-killing abilities, and, hence, for their cancer-cell-killing abilities. Preferably, this inhibition also has a indirect effect of lowering formation of metabolites that build up during or after treatment with anthracycline cancer drugs, said metabolites being ones that are believed to disrupt heart muscle processes and therefore to interfere with heart function. Therefore, by using preferred embodiments of the invented compositions and/or methods, much less anthracycline drug is expected to be needed to achieve the desired killing of cells, and much less cardiotoxic metabolite will be produced over the duration of the cancer treatment.

The invented compositions comprise compounds having at least one aryl (preferably phenyl) group, wherein at least one of said at least one aryl/phenyl group comprises one or more halogen, pseudo-halogen, and/or hydroxyl group. In the preferred embodiments disclosed herein, the compositions comprise compounds having at least two aryl (preferably phenyl) groups, wherein at least one of said at least two aryl/phenyl groups comprises one or more halogen, pseudo-halogen, and/or hydroxyl group.

In especially-preferred embodiments, two halogenated, pseudo-halogenated and/or hydroxylated aryl/phenyl groups are connected by a bridging carbon, oxygen, sulfur, nitrogen, or derivative of carbon, oxygen, sulfur, or nitrogen, wherein at least one of said aryl/phenyl groups comprises at least one halogen, pseudo-halogen, or hydroxyl group. Especially-preferred embodiments comprise one or more biphenyl compounds selected from the group consisting of: triclosan, hexachlorophene, dichlorophene, bithionol, bithionol sulfoxide, and derivatives thereof. The biphenyl compounds may be administered to a human (or other mammal) in a pharmaceutical composition also comprising at least one anthracycline compound, or may be administered separately from the at least one anthracycline compound either at the same time as the anthracycline(s), or any different time found to be effective for inhibiting formation of the anthracycline metabolites.

Therefore, an object of the preferred embodiments is to inhibit one or more of the members of the aldo-keto reductase and/or short chain dehydrogenase/reductase protein superfamilies that catalyze conversion of anthracycline to anthracycline metabolites. The preferred embodiments inhibit human carbonyl reductase and are expected to produce the synergistic effects of reducing cardiotoxicity from anthracycline chemotherapy and also lowering dosages of the anthracycline drug that will be effective for cancer-cell-killing.

BRIEF DESCRIPTION OF THE DRAWINGS

FIG. 2 is a representation of a carbonyl reductase—NADPH mechanism for reducing the anthracycline daunorubicin to the anthracycline alcohol metabolite daunorubicinol.

FIGS. 3A-E illustrate: 3A. Bithionol, 3B. Bithionol Sulfoxide, 3C. Hexachlorophene, 3D. Dichlorophene, and 3E. Triclosan. In the representation of a general structure of FIG. 3F, $R_1$=C, S, O, N and all derivatives; $R_2$=hydrogen, halogen, alcohol, pseudohalogen; and carbons in the phenyl ring may also be replaced by N, S, and/or O.

FIG. 7 describes inhibition patterns seen with inhibitors dichlorophene, hexachlorophene, and triclosan wherein $K_{IS}$ and $K_{II}$ stand for the slope and intercept inhibition constants, respectively.

DESCRIPTION OF THE PREFERRED EMBODIMENTS

Referring to the figures, there are shown several, but not the only, embodiments of the invented composition of matter and methods for enhancing the efficacy of anthracycline drug cancer treatment and/or limiting side-effects thereof. The preferred methods and compositions of matter may maintain effective concentrations of anthracycline(s) during cancer treatment, by preventing or lowering conversion of the anthracycline(s) to metabolites that are less effective or ineffective as cancer-cell-killing species. The preferred methods and compositions may also prevent or lower the potentially life-threatening cardiotoxicity associated with anthracycline chemotherapy for cancer patients.

Some embodiments of the invention may include compositions, and/or methods of using the compositions in cancer treatment, that comprise one aryl (preferably phenyl) group, for example, a halogenated aryl group, oximino(2,4-difluorophenyl)acetonitrile, oximino(2,6-difluorophenyl)acetonitrile, oximino(2,5-difluorophenyl)acetonitrile, oximino(2-chloro-6-fluorophenyl)acetonitrile, oximino(2,4-dichlorophenyl)acetonitrile, oximino(2,6-dichlorophenyl)acetonitrile, and/or mixtures of two or more thereof, as disclosed in Patent Application Ser. No. 60/830,293 and Ser. No. 11/776,536. However, embodiments of the invention that are expected to show superior results in the treatment of cancer may be described as those comprising at least two (preferably two) aryl or phenyl groups, and, especially, those that are disclosed in Patent Application Ser. No. 60/776,269 and Ser. No. 11/711,490 and that are disclosed herein. Therefore, the preferred compounds that are expected to provide superior results for use in the above-described prevention or lowering of anthracycline conversion have at least two aryl (preferably phenyl) groups, wherein at least one of the aryl/phenyl groups has at least one halogen, pseudo-halogen or a hydroxyl group as a substituent. Pseudo-halogens may include binary inorganic compounds of the general form XY, where X is a cyanide, cyanate, or thiocyallate and where Y is any of X or a true halogen, including but not limited to cyanogen ($(CN)_2$) and iodine cyanide (ICN). Preferably, biphenyl compounds that are halogenated or pseudo-halogenated also comprise at least one hydroxyl group.

Figure 1:
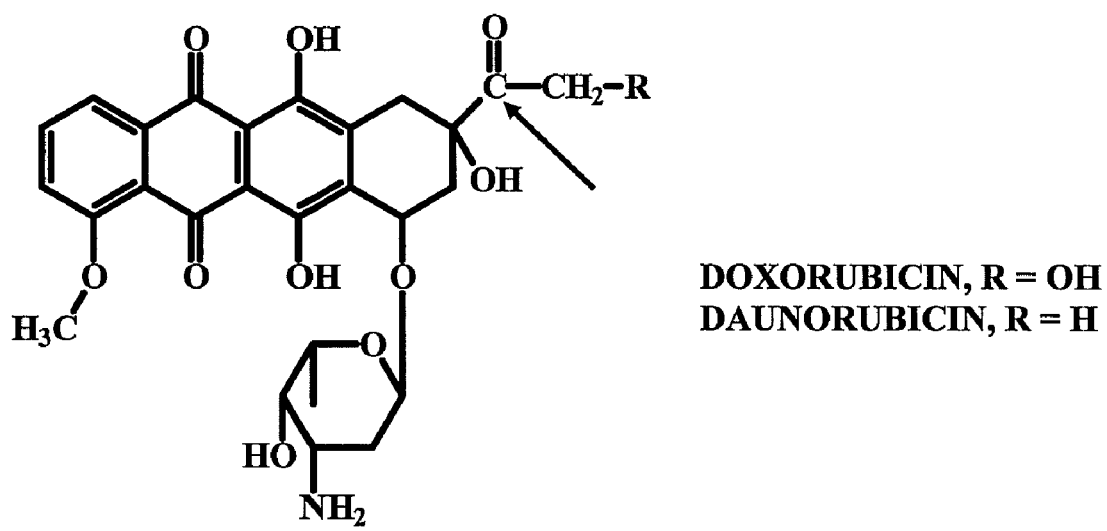
FIG. 1 is a representation of an anthracycline compound, which may be doxorubicin (R=OH) or daunorubicin (R=H), wherein the arrow designates the carbon at position 13.
Figure 3B:
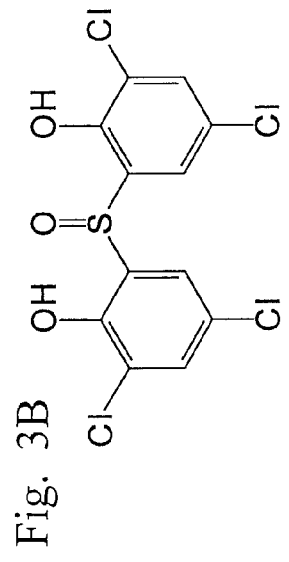
FIGS. 3A-F show the chemical structures of several biphenyl inhibitors (FIGS. 3A-E) of carbonyl reductase according to embodiments of the invention and a representation of a general structure (FIG. 3F) expected to lead to other carbonyl reductase inhibitors with the scope of the invention.
Figure 3D:
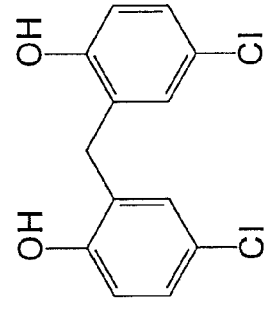
Figure 3F:
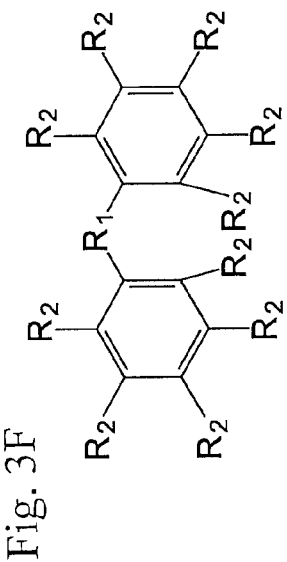
Figure 3A:
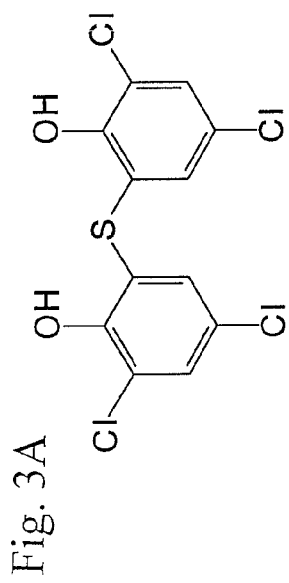
Figure 3C:
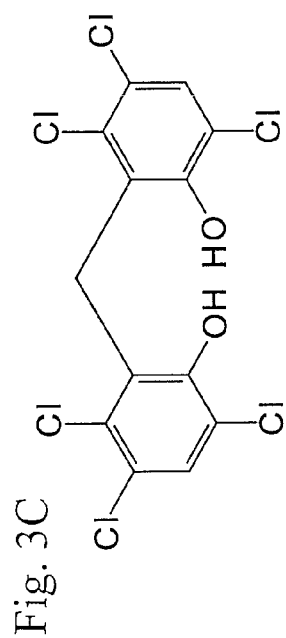
Figure 3E:
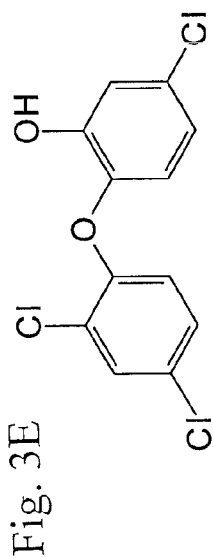

The especially-preferred embodiments comprise one or more substituted biphenyl compounds, and preferably one or more of the following compounds: triclosan, hexachlorophene, dichlorophene, and, as previously described in Patent Application Ser. No. 60/776,269 and Ser. No. 11/711, 490, bithionol, bithionol sulfoxide, and derivatives thereof. See FIGS. 3A-E. Also, it is expected that derivatives or analogs of these compounds may be effective in the place of one or more of these compounds, or as a supplement to one or more of these compounds. Considering the structures of the triclosan, hexachlorophene, and dichlorophene and bithionol and bithionol sulfoxide from patent application Ser. No. 11/711,490, an overall general structure (biphenyl compound) for possible carbonyl reductase inhibitors is envisioned. This biphenyl compound general structure is depicted in FIG. 3F and compounds fitting this general structure are also expected to prevent or hinder anthracycline conversion in embodiments of the invention.

The compounds and general structure illustrated in FIGS. 3A-F may further be described by the following Table 1:

TABLE 1

| Figure No. | Names |
|---|---|
| 3A | Bithionol, 2,2'-Thio-bis(4,6-dichlorophenol), Bis(2-hydroxy-3,5-dichlorophenyl) sulfide |
| 3B | Bithionol Sulfoxide, 2,2'-Sulfinyl-bis (4,6-dichlorophenol) |
| 3C | Hexachlorophene, 2,2'-Methylenebis(3,4,6-trichlorophenol) |
| 3D | Dichlorophene, Bis(5-chloro-2-hydroxphenyl)methane, Dichlorophen |
| 3E | Triclosan, 5-Chloro-2-(2,4-dichlorophenoxy)phenol, Irgasan |
| 3F | A General Structure, wherein $R_1$ = C, S, O, N and/or all derivatives; wherein $R_2$ = hydrogen, halogen, alcohol (hydroxyl), and/or pseudohalogen; and wherein carbons in the phenyl ring may be replaced by N, S and/or O. (Note that, while the ring structures of FIG. 3F are portrayed in the conventional manner as six- carbon ring structures, one or more of the carbons of one or both of said six-carbon ring structures may be replaced by nitrogen, sulfur, and/or oxygen, and may not have hydrogen or substituent groups). |

It may be noted that carbon of the aryl/phenyl rings shown in FIG. 3F may be replaced by N, S, and/or O. It may also be noted that one or more halogen, pseudo-halogen and/or alcohol groups may be substituent groups bound to all or some of the carbons of one or both of the aryl/phenyl rings of the preferred compounds, but that carbon sites (carbons of the aryl-phenyl rings) may also have no substituent group (hence, "unsubstituted") and would comprise hydrogen bound to said carbon sites, as will be understood by one skill in the art. The atom/compound bridging the aryl/phenyl groups may be carbon, oxygen, sulfur, nitrogen, or derivative of carbon, oxygen, sulfur, or nitrogen.

Use of Preferred Compositions as Enzyme Inhibitors

Human "carbonyl reductase" is believed to comprise several isoenzymes, which are members of the short-chain dehydrogenase/reductase superfamily and monomeric or tetrameric with subunit molecular weight of approximately 30 kDa. Carbonyl reductase uses NADPH, and may have physiological roles including quinone detoxification or other roles.

Multiple studies point to human carbonyl reductase (such as carbonyl reductase 1) having a role in the production of the anthracycline metabolites believed to cause cardiotoxic side effects in cancer patients either near the time of the chemotherapy or at some later time. This disease or condition of cardiotoxicity related to anthracycline drugs is briefly described above in the Related Art Section. Also, see FIG. 2 for one example of a mechanism of carbonyl reductase reduction of an anti-cancer anthracycline to a cardiotoxic alcohol metabolite. C13-hydroxy-metabolites are believed to be the principle cardiotoxic agents resulting from enzyme action upon anthracyclines.

In addition, because the anthracycline metabolite(s) are believed to not possess the anti-neoplastic properties of the parent anthracycline(s), carbonyl reductase may also contribute to anthracycline drug resistance. In other words, carbonyl reductase may lower anthracycline concentrations in the human body by catalyzing conversion of the anthracycline, and, hence, may lower the amount of cancer cells killed by a given dose of anthracycline drug.

Several biphenyl compounds, namely, triclosan, hexachlorophene, dichlorophene and those identified in Ser. Nos. 60/776,269 and Ser. No. 11/711,490, have been shown by the inventor to inhibit carbonyl reductase, and are envisioned to allow an increase in anthracycline chemotherapy by offsetting the negative side effects of this chemotherapy. Also, as discussed above, the preferred compositions and methods may decrease anthracycline drug resistance, further improving the results of anthracycline chemotherapy.

Figure 4:
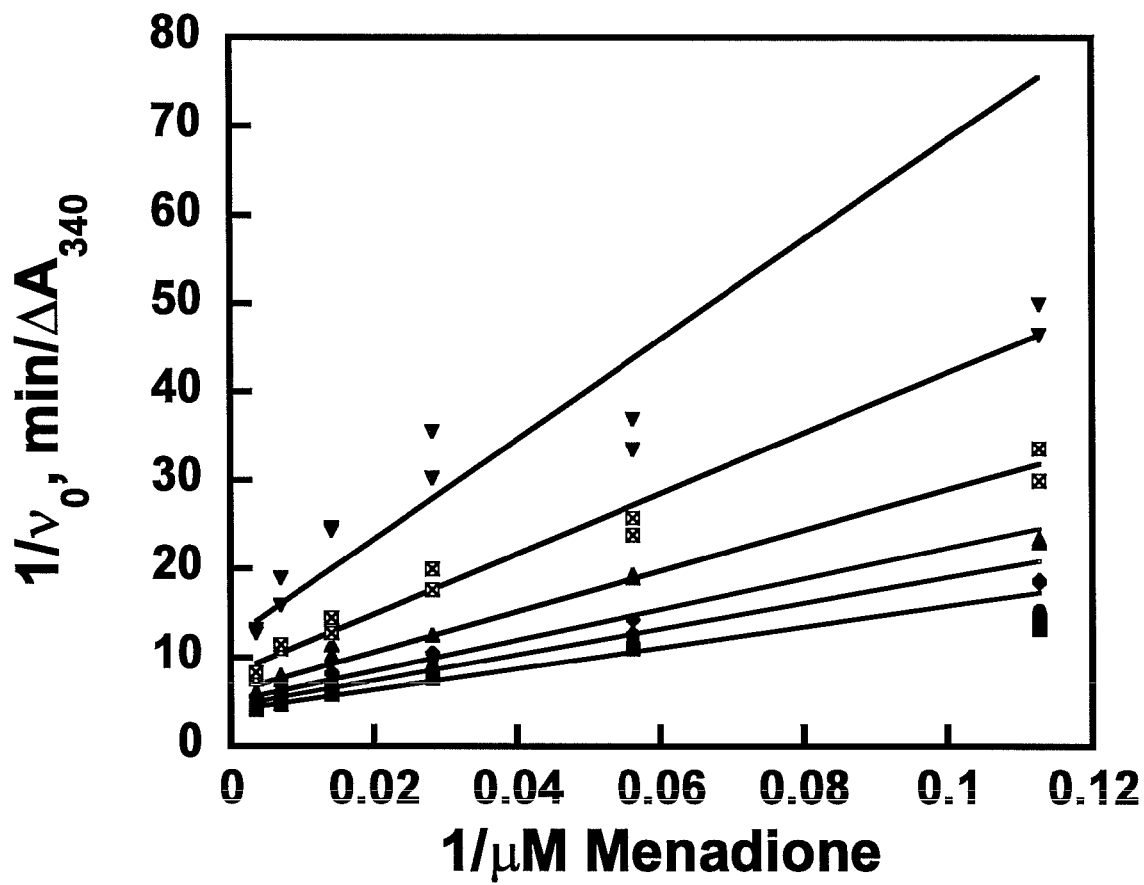
FIG. 4 is a graph showing that dichlorophene is a noncompetitive inhibitor against menadione, when the NADPH concentration is fixed at 50 μM.
Figure 5:
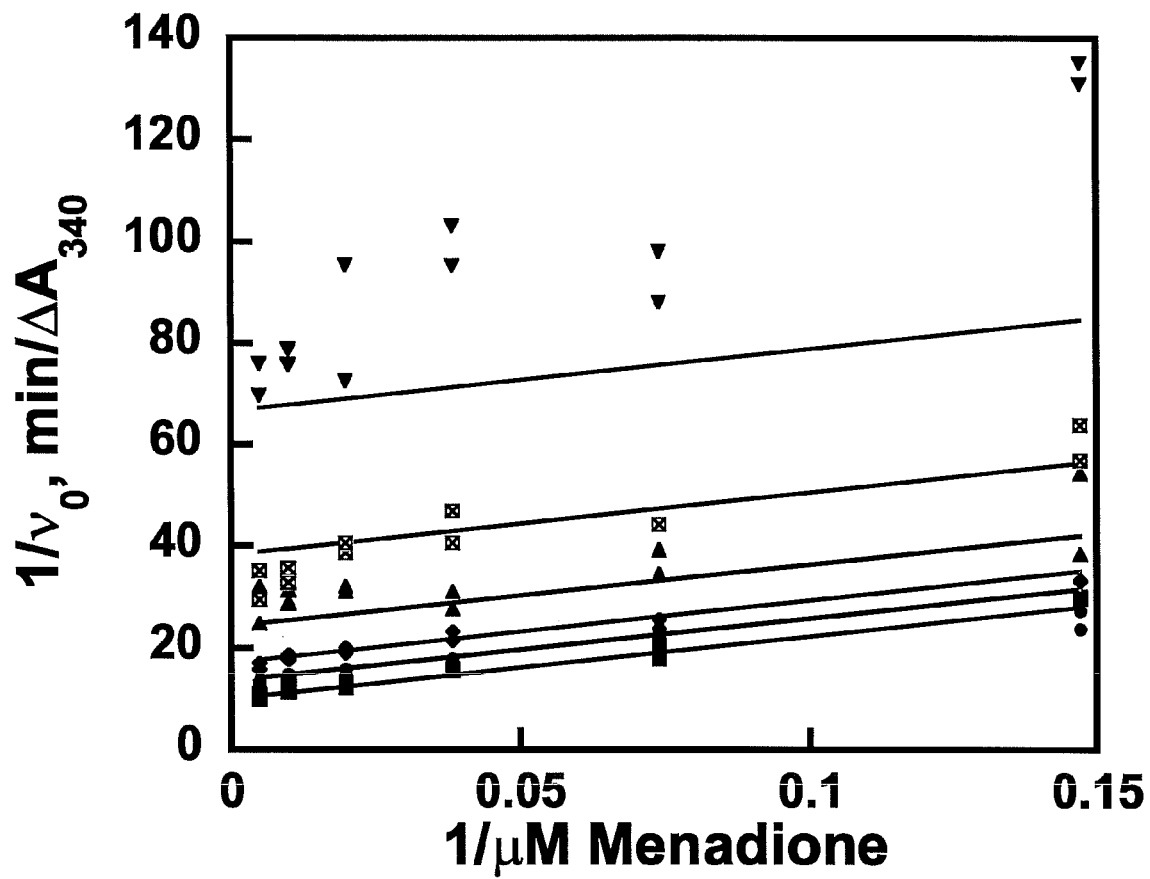
FIG. 5 is a graph showing that hexachlorophene is an uncompetitive inhibitor against menadione, when the NADPH concentration is fixed at 50 μM.
Figure 6:
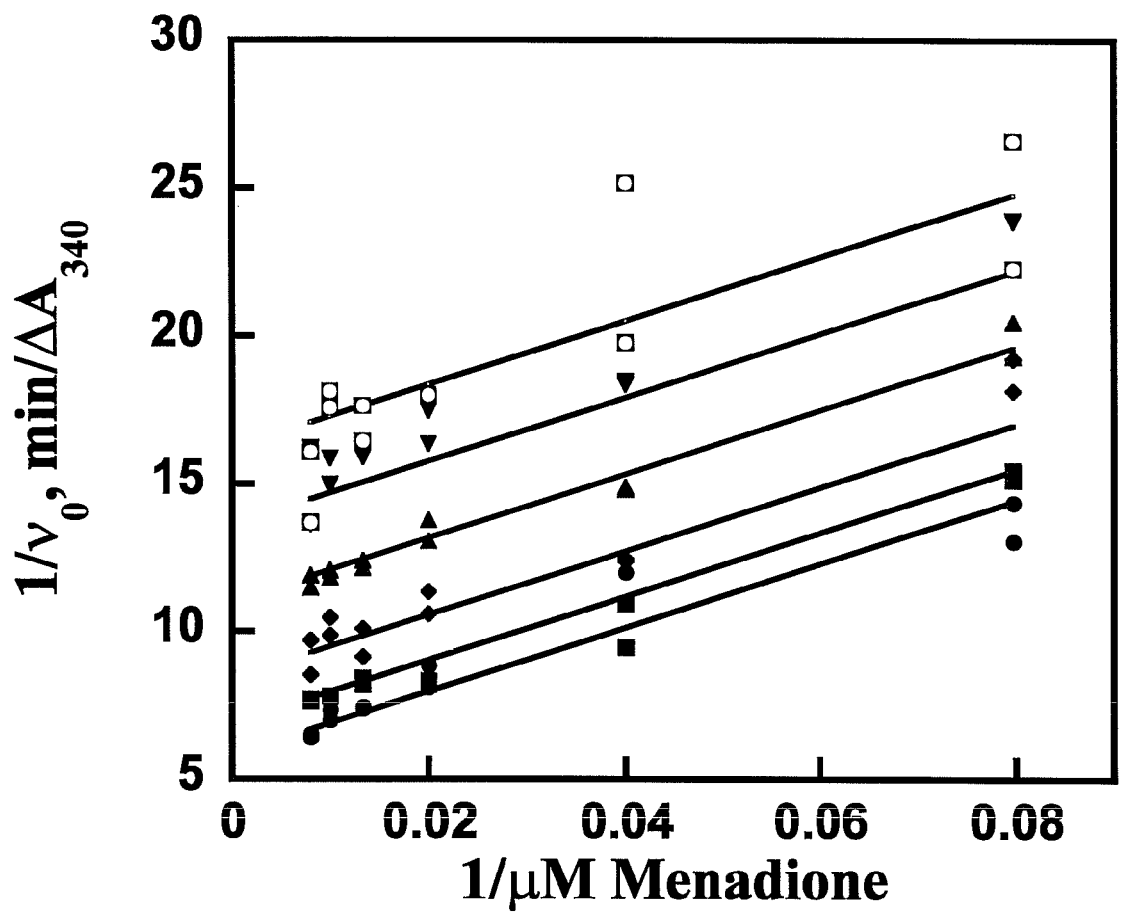
FIG. 6 is a graph showing that triclosan is an uncompetitive inhibitor against menadione, when the NADPH concentration is fixed at 50 μM.

Specifically, referring to FIGS. 4-6, triclosan, hexachlorophene, and dichlorophene have been shown by the inventors to be uncompetitive inhibitors (noncompetitive for dichlorophene) carbonyl substrates, with inhibition constant values ranging from 0.23-78 µM. These preferred compounds have been seen to exhibit inhibition patterns suggestive of binding to multiple enzyme forms, which may mean that increased anthracycline dosages may not overcome the inhibition. See FIGS. 4-6, which comprise data from laboratory testing using menadione. Menadione could be replaced by anthracyclines or other carbonyl-containing substrates, so that menadione may be considered a substitute or surrogate for anthracyclines or other carbonyl-containing substrates in these studies, and, hence, indicative of expected performance regarding anthracyclines.

Triclosan, hexachlorophene, and dichlorophene are known antibiotics. For examples see the following literature:

Kim, Woo-Jae; Oh, Nam-Hun; Park, Seung-Kyu; Kim, Jeong-Cheol. Antimicrobial composition comprising silver zeolite, Houttuynia cordata extract and triclosan, filter for indoor air quality applying the same and manufacturing method thereof. PCT Int. Appl. (2007), 16 pp. CODEN: PIXXD2 WO 2007074957 A1 20070705 CAN 147:125938 AN 2007:728884;

Belcheva, Nadya; Kennedy, John. Antimicrobial medical devices with adherence-enhancing agents. U.S. Pat. Appl. Publ. (2007), 8 pp. CODEN: USXXCO US 2007207189 A1 20070906 AN 2007:993759.

Knappenberger, Kyle; Martin, Lisa; Malchesky, Paul S. Organic biocidal decontamination compositions. PCT Int. Appl. (2006), 19 pp. CODEN: PIXXD2 WO 2006085975 A2 20060817 CAN 145:235978 AN 2006:817656.

Also triclosan, hexachlorophene, and dichlorophene are known anti-neoplastic agents. See, for example:

Fischer, Frank J.; Miller, Jessica Watts; Andrews, Marvin O. Implantable medical device with anti-neoplastic drug. U.S. Pat. Appl. Publ. 200652757 (Mar. 9, 2006), 12 pp., Oh, Sang Taek. Pharmaceutical composition for treating cancer containing hexachlorophene capable of inhibiting wnt/beta-catenin response transcription. Repub. Korean Kongkae Taeho Kongbo (2006), No pp. given. CODEN: KRXXA7 KR 2006124031 A 20061205 CAN 147:79443 AN 2007:703062.

Westwick, John K.; Yu, Helen; Owens, Stephen; MacDonald, Marnie L. Drugs for the treatment of neoplastic disorders. (Odyssey Thera, Inc., USA). U.S. Pat. Appl. Publ. 20060009506 (Jan. 12, 2006), 21 pp. CODEN: USXXCO US 2006009506 A1 20060112.

To the inventors' knowledge, however, triclosan, hexachlorophene, or dichlorophene have not been used in any process for improving efficacy of drugs used in cancer treatment of for treating or preventing side effects of cancer treatment or cardiotoxicity. Further, to the inventors' knowledge, triclosan, hexachlorophene, or dichlorophene have not been previously reported as carbonyl reductase inhibitors. The inventors believe that said effective and safe doses may be found without undue experimentation by one of skill in the art after reading this disclosure, especially in view of literature regarding known uses (as anti-biotics and anti-neoplastic agents) of triclosan, hexachlorophene, and dichlorophene.

In use, one or more of the preferred compounds, triclosan, hexachlorophene, dichlorophene and compounds with the biphenyl compound core or "general" structure (FIG. 3F) may be used in a pharmaceutical composition, which may also comprise one or more of the anthracycline drugs and/or other chemotherapy drugs or other medicines that may be beneficial to the cancer patient. Preferably, the triclosan, hexachlorophene, dichlorophene and compounds with the biphenyl compound core structure (FIG. 3F) and anthracycline compositions are given at levels that produce the desired anti-cancer effects without the cardiotoxicity side effects. Therefore, the relative compositions may be changed for different anthracyclines and/or for different patients and/or for different cancers. The methods include treatment of, or treatment of side effects, for all cancers for which anthracyclines are used. Embodiments of the invention therefore include a pharmaceutical composition comprising at least one anthracycline compound and triclosan, hexachlorophene, dichlorophene and compounds with the general core structure depicted in FIG. 3F or a mixture of some or all thereof. The inventor envisions that there may be analogs or derivatives of triclosan, hexachlorophene, dichlorophene and compounds with the biphenyl compound core structure (FIG. 3F) that also may be effective in compositions and methods of the invention. For example, the compositions may include anthracycline compounds selected from the group consisting of adriamycin/doxorubicin, daunorubicin/daunomycin, epirubicin, idarubicin, and a mixture of two or more thereof.

While the preferred patients are humans, animals may also benefit from the compositions and methods. Embodiments of the invented method may be for preventing or treating cardiotoxicity associated with anthracycline cancer chemotherapy in a mammal in need thereof, wherein the method comprises administering to the mammal a composition comprising an effective amount of a pharmaceutical composition comprising at least one anthracycline compound and at least one compound or mixture selected from the group consisting of triclosan, hexachlorophene, dichlorophene, compounds with the biphenyl compound core structure (FIG. 3F), a mixture of some of all of said compounds, an analog and/or derivative of said compounds, and mixtures of two or more thereof. Effective amounts will be determined by methods known to those of skill in the art. Examples of anthracycline compounds include adriamycin/doxorubicin), daunorubicin/daunomycin, epirubicin, idarubicin, and a mixture of two or more thereof.

Instead of, or in addition to, administering a pharmaceutical composition including both anthracycline(s) and triclosan, hexachlorophene, dichlorophene and compounds with the biphenyl compound core structure (FIG. 3F), separate pharmaceutical compositions may be used. For example, methods may include preventing or treating a disease or condition associated with carbonyl reductase in a mammal in need thereof by administering to the mammal a first pharmaceutical composition comprising at least one anthracycline compound; and also administering to the mammal a second pharmaceutical composition comprising triclosan, hexachlorophene, dichlorophene and compounds with the biphenyl compound core structure (FIG. 3F), or a mixture of some or all thereof. The first and second pharmaceutical compositions may be administered at the same time, or may be administered at nearly the same time (for example, within 15 minutes or less), or preferably within a few hours of each other (for example, within 2 hours or less). It may be beneficial to treat the patient with triclosan, hexachlorophene, dichlorophene, and/or compounds with the biphenyl compound core structure (FIG. 3F) prior to anthracycline therapy (for example, two hours or less prior to anthracycline treatment), to block carbonyl reductase before administration of the anthracycline drug(s).

Inhibition Data

Triclosan, hexachlorophene, and dichlorophene were tested as possible inhibitors for carbonyl reductase. Triclosan and hexachlorophene (See FIGS. 3C and E) were found to be uncompetitive inhibitors against the carbonyl substrate, with triclosan being one of the most potent carbonyl reductase inhibitors known to date. Dichlorophene (See FIG. 3D) was found to be a noncompetitive inhibitor of carbonyl reductase at 50 μM NADPH and an uncompetitive inhibitor at 300 μM NADPH. See FIG. 4-6, portraying the 1/rate vs. 1/menadione concentration studies done with dichlorophene, hexachlorophene, and triclsosan, respectively. The data in FIGS. 4-6 show changes in y-intercept, while only the data in FIG. 4, show changes in slope. To those skilled in the art, it will be evident that dichlorophene exhibits noncompetitive inhibition against menadione, while hexachlorophene and tricosan exhibit uncompetitive inhibition against varied menadione. As shown in FIG. 7, triclosan has the lowest inhibition constant (0.23 μM) and is therefore the over 52 times more potent in its inhibition than is hexachlorophene. Therefore, while compositions comprising triclosan are preferred, compositions comprising hexachlorophene and dichlorophene are also included in embodiments of the invention and are also expected by the inventors to be beneficial in the methods of the invention. The inhibition patterns noted in FIG. 7 are further described/explained as follows:

a. Regarding note "a" in FIG. 7: Studies were done with a fixed NADPH concentration of μM 50, varied menadione concentrations ranging from 12 to 125 μM in 100 mM sodium phosphate buffer, pH=7.0.

b. Regarding note "b" in FIG. 7: The data fit best to the uncompetitive inhibition model $$v_0 = \frac{VA}{A\left(1 + \frac{I}{K_{ii}}\right) + K_m}$$

wherein A is the concentration of menadione, I is the inhibitor concentration, V is the maximal velocity, $K_m$ is the Michaelis constant for mendadione and $K_{ii}$ is the intercept inhibition constant.

c. Regarding note "c" in FIG. 7: The data fit best to the noncompetitive inhibition model $$v_0 = \frac{VA}{A\left(1 + \frac{I}{K_{ii}}\right) + K_m\left(1 + \frac{I}{K_{is}}\right)}$$

wherein A is the concentration of menadione, I is the inhibitor concentration, V is the maximal velocity, $K_m$ is the Michaelis constant for menadione, $K_{ii}$ is the intercept inhibition constant, and $K_{is}$ is the slope inhibition constant.

d. Regarding note "d" is FIG. 7: The study was done with a fixed NADPH concentration of 300 μM and varied menadione as described above.

Figure 8:
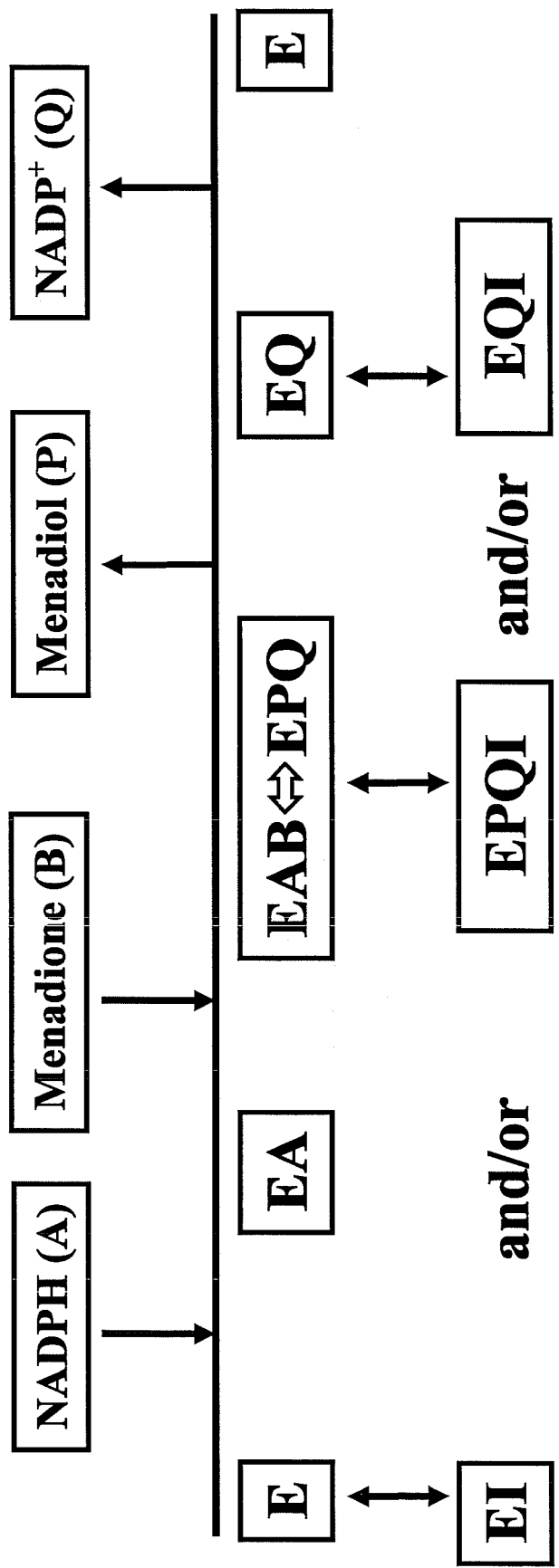
FIG. 8 summarizes data showing that all of the inhibitors bind to enzyme forms distinct from those to which menadione binds, as determined from inhibition studies such as those represented in FIGS. 4-7. The inhibitors (represented by "I") dichlorophene, hexachlorophene, and triclosan may bind to free enzyme, ternary and/or the enzyme-NADP$^+$ binary complex. Enzyme (CR) is represented by "E". Menadione could be replaced by anthracyclines or other carbonyl-containing substrates, so that menadione may be considered a substitute or surrogate for anthracyclines or other carbonyl-containing substrates in these studies.

From the above inhibition patterns, the inhibitors triclosan, hexachlorophene, and dichlorophene most likely bind to the free enzyme and/or the enzyme-NADP$^+$ binary complex and/or the enzyme-menadione-NADPH ternary complex, as illustrated in FIG. 8. It is expected that substrate carbonyls should not appreciably compete against the preferred inhibitors at these sites. Thus, said preferred inhibitors according to the invention are expected to remain available for, and will effectively carry out, inhibition of the mechanism that would otherwise result in lower efficacy of anthracycline(s) drugs and in cardiotoxic compounds.

Figure 9:
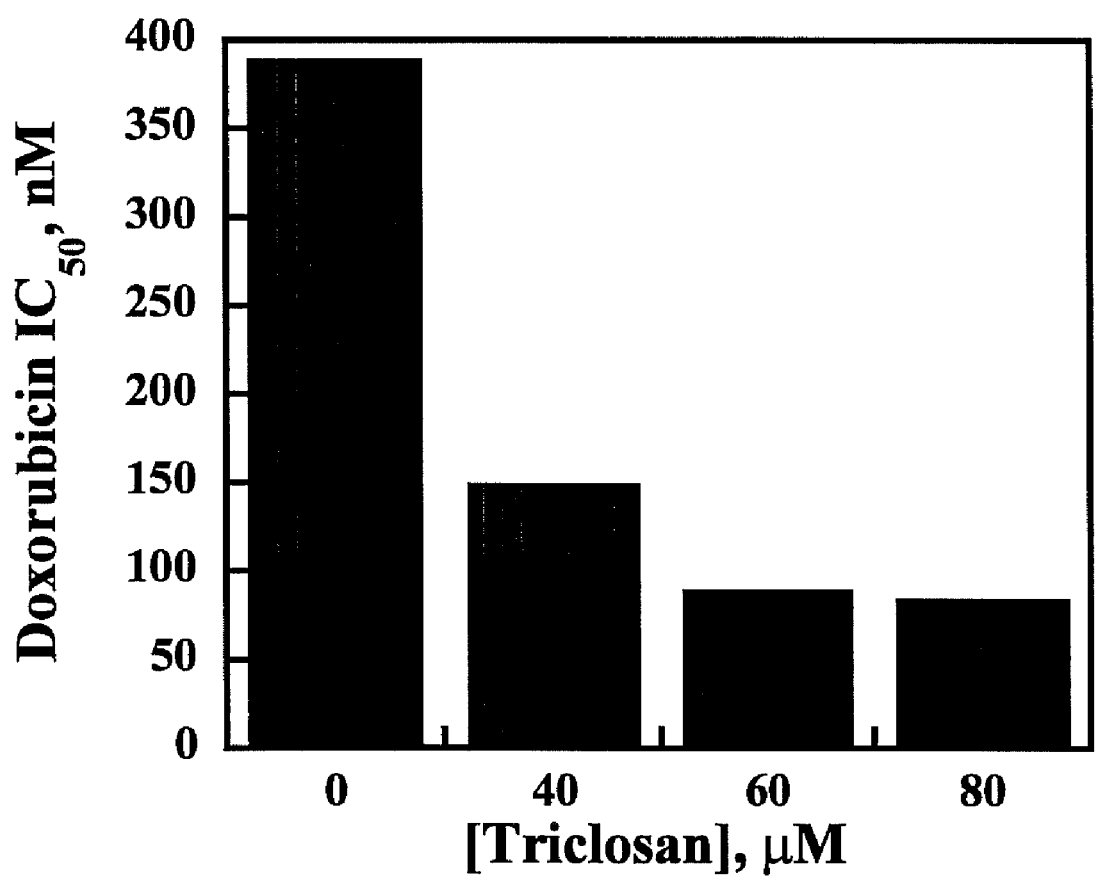
FIG. 9 shows a graph indicating that addition of increasing concentrations of triclosan lowers the $IC_{50}$ of doxorubicin in killing breast cancer cells (MDA cell line). Cell viability was determined by uptake of alomar blue.

In a breast cancer cell line, MDA, triclosan was shown to decrease the doxorubicin $IC_{50}$ for cell killing. It appears from the graph in FIG. 9, that it is possible to increase the cell killing efficacy of doxorubicin by about 4-fold in breast cancer cells. FIG. 9 illustrates the large decrease in $IC_{50}$ of Doxorubicin when 40 μM triclosan is used compared to 0 (zero) μM triclosan (approximately 380 nM reduced to approximately 145 nM), and the additional but smaller decrease in $IC_{50}$ of Doxorubicin when 60 μM triclosan is used compared to 40 μM triclosan (approximately 145 nM reduced to approximately 95 nM), and the additional but even smaller decrease in $IC_{50}$ of Doxorubicin when 80 μM triclosan is used (approximately 95 nM reduced to approximately 85 nM). The reduction in $IC_{50}$ for doxorubicin appears to have a lower limit of about 85 nM when 80 μM triclosan is used.

Although this invention has been described above with reference to particular means, materials and embodiments, it is to be understood that the invention is not limited to these disclosed particulars, but extends instead to all equivalents within the broad scope of the following claims.

The invention claimed is:

1. A pharmaceutical composition comprising at least one anthracycline compound selected from the group consisting of adriamycin, daunomycin, daunorubicin, doxorubicin, epirubicin, idarubicin, and mixtures of two or more thereof, and at least one carbonyl reductase enzyme inhibitor compound selected from the group consisting of triclosan, hexachlorophene, dichlorophene, and mixtures of two or more thereof, and wherein said at least one enzyme inhibitor exhibits a $K_{II}$ value in the range of 0.23-78 microMolar.

2. A composition as in claim 1 wherein said carbonyl reductase inhibitor compound is triclosan and exhibits a $K_{II}$ value of 0.23 microMolar.

3. A method for reducing effective doses of anthracycline effective for cancer chemotherapy in a human in need thereof, the method comprising:
administering to the human a composition comprising an effective amount of a pharmaceutical composition comprising at least one anthracycline compound selected from the group consisting of adriamycin, daunomycin, daunorubicin, doxorubicin, epirubicin, idarubicin, and mixtures of two or more thereof, and at least one enzyme inhibitor lowering effective doses of anthracycline, said at least one enzyme inhibitor comprising a human carbonyl reductase enzyme inhibitor selected from the group consisting of triclosan, hexachlorophene, dichlorophene, and mixtures of two or more thereof, and exhibits a $K_{II}$ value in the range of 0.23-78 microMolar.

4. The method of claim 3, further comprising reducing cardiotoxicity associated with anthracycline cancer chemotherapy by means of said at least one enzyme inhibitor inhibiting human carbonyl reductase.

5. A method for improving efficacy of anthracycline chemotherapy by inhibiting carbonyl reductase in a human, the method comprising:
administering to the human a first pharmaceutical composition comprising at least one anthracycline compound selected from the group consisting of adriamycin, daunomycin, daunorubicin, doxorubicin, epirubicin, idarubicin, and mixtures of two or more thereof; and,
also administering to the human a second pharmaceutical composition comprising an enzyme inhibitor comprising at least one carbonyl reductase enzyme inhibitor compound, wherein said at least one carbonyl reductase enzyme inhibitor compound is selected from the group consisting of triclosan, hexachlorophene, dichlorophene, and mixtures of two or more thereof, and wherein said at least one enzyme inhibitor exhibits a $K_{II}$ value in the range of 0.23-78 microMolar.

6. A method as in claim 5, wherein said second pharmaceutical composition is administered at the same time as said first pharmaceutical composition.

7. A method as in claim 5, wherein said second pharmaceutical composition is administered within two hours or less of said first pharmaceutical composition.

8. A method as in claim 5, wherein said second pharmaceutical is administered prior to the first pharmaceutical composition.

9. A method as in claim 5, wherein said second pharmaceutical is administered after the first pharmaceutical composition.

* * * * *